United States Patent
Zhu et al.

(10) Patent No.: US 10,247,854 B2
(45) Date of Patent: Apr. 2, 2019

(54) METHODS AND SYSTEMS FOR DETECTING WEATHER CONDITIONS USING VEHICLE ONBOARD SENSORS

(71) Applicant: Waymo LLC, Mountain View, CA (US)

(72) Inventors: Jiajun Zhu, Sunnyvale, CA (US); Dmitri Dolgov, Mountain View, CA (US); Dave Ferguson, San Francisco, CA (US)

(73) Assignee: Waymo LLC, Mountain View, CA (US)

( * ) Notice: Subject to any disclaimer, the term of this patent is extended or adjusted under 35 U.S.C. 154(b) by 75 days.

(21) Appl. No.: 15/449,097

(22) Filed: Mar. 3, 2017

(65) Prior Publication Data
US 2017/0176641 A1 Jun. 22, 2017

Related U.S. Application Data

(63) Continuation of application No. 13/888,634, filed on May 7, 2013, now Pat. No. 9,632,210.

(51) Int. Cl.
*G06F 19/00* (2018.01)
*G01W 1/00* (2006.01)
(Continued)

(52) U.S. Cl.
CPC .......... *G01W 1/00* (2013.01); *G01N 21/4738* (2013.01); *G01S 17/023* (2013.01); *G01S 17/87* (2013.01);
(Continued)

(58) Field of Classification Search
CPC ....... G01S 17/936; G01S 17/023; G01S 17/95
(Continued)

(56) References Cited

U.S. PATENT DOCUMENTS

| 6,061,015 A | 5/2000 | Sugimoto |
| 6,535,141 B1 * | 3/2003 | Doherty ................. A01C 17/00 340/580 |

(Continued)

FOREIGN PATENT DOCUMENTS

| EP | 1302784 | 4/2003 |
| EP | 1500954 | 1/2005 |

(Continued)

OTHER PUBLICATIONS

Supplementary European Search Report prepared by the European Patent Office in Application No. EP 14 78 3297, dated Sep. 29, 2016.

(Continued)

*Primary Examiner* — Edward Raymond
(74) *Attorney, Agent, or Firm* — McDonnell Boehnen Hulbert & Berghoff LLP

(57) ABSTRACT

Example methods and systems for detecting weather conditions using vehicle onboard sensors are provided. An example method includes receiving laser data collected for an environment of a vehicle, and the laser data includes a plurality of laser data points. The method also includes associating, by a computing device, laser data points of the plurality of laser data points with one or more objects in the environment, and determining given laser data points of the plurality of laser data points that are unassociated with the one or more objects in the environment as being representative of an untracked object. The method also includes based on one or more untracked objects being determined, identifying by the computing device an indication of a weather condition of the environment.

23 Claims, 7 Drawing Sheets

(51) Int. Cl.
*G01W 1/14* (2006.01)
*G01N 21/47* (2006.01)
*G01S 17/02* (2006.01)
*G01S 17/87* (2006.01)
*G05D 1/00* (2006.01)
*G05D 1/02* (2006.01)
*H04N 7/18* (2006.01)

(52) U.S. Cl.
CPC ............ *G01W 1/14* (2013.01); *G05D 1/0088* (2013.01); *G05D 1/024* (2013.01); *G05D 1/0246* (2013.01); *G05D 1/0257* (2013.01); *G05D 1/0276* (2013.01); *H04N 7/183* (2013.01)

(58) Field of Classification Search
USPC ..................................... 702/3, 4, 6, 182–185
See application file for complete search history.

(56) References Cited

U.S. PATENT DOCUMENTS

| | | | |
|---|---|---|---|
| 6,812,855 B1 * | 11/2004 | Sudou | ............. G08G 1/096716 340/539.1 |
| 7,142,150 B2 | 11/2006 | Thackray | |
| 7,272,474 B1 | 9/2007 | Stentz et al. | |
| 7,565,230 B2 | 7/2009 | Gardner et al. | |
| 7,741,961 B1 | 6/2010 | Rafii et al. | |
| 7,983,838 B1 * | 7/2011 | Mislan | ...................... E02B 5/06 701/466 |
| 8,060,308 B2 | 11/2011 | Breed | |
| 2003/0164689 A1 | 9/2003 | Schmitt et al. | |
| 2008/0042812 A1 | 2/2008 | Dunsmoir et al. | |
| 2009/0030605 A1 | 1/2009 | Breed | |
| 2009/0032712 A1 | 2/2009 | Robert et al. | |
| 2009/0322872 A1 | 12/2009 | Muehlmann et al. | |
| 2010/0217529 A1 | 8/2010 | Stroila et al. | |
| 2010/0253539 A1 | 10/2010 | Seder et al. | |
| 2011/0060478 A1 | 3/2011 | Nickolaou | |
| 2012/0069181 A1 | 3/2012 | Xue et al. | |
| 2012/0083982 A1 | 4/2012 | Bonefas et al. | |
| 2012/0288145 A1 | 11/2012 | Kido | |
| 2012/0293317 A1 | 11/2012 | Hanna et al. | |
| 2014/0336935 A1 | 11/2014 | Zhu et al. | |

FOREIGN PATENT DOCUMENTS

| | | |
|---|---|---|
| JP | 08-184675 | 7/1996 |
| JP | 2000 121730 | 4/2000 |
| JP | 2002-257934 | 9/2002 |
| JP | 2005-141517 | 6/2005 |
| JP | 2005-180994 | 7/2005 |
| JP | 2010-223685 | 10/2010 |
| JP | 2013-020288 | 1/2013 |
| WO | WO 03/000513 | 1/2003 |
| WO | WO 2014/047250 | 3/2014 |

OTHER PUBLICATIONS

International Preliminary Report on Patentability and Written Opinion prepared by the Korean Patent Office in International Patent Application Serial No. PCT/US2014/033125, dated Oct. 22, 2015.
International Search Report and Written Opinion prepared by the Korean Patent Office in International Patent Application Serial No. PCT/US2014/033125, dated Aug. 21, 2014.
Bronte, et al., "Fog Detection System Based on Computer Vision Techniques", Intelligent Transportation Systems, 2009. ITSC '09. 12th International IEEE Conference, Date: Oct. 4-7, 2009.
Hautiere, et al., "Real-time disparity contrast combination for onboard estimation of the visibility distance", IEEE Transactions on Intelligent Transportation Systems, vol. 7, No. 2, Jun. 2006, pp. 201-212.

* cited by examiner

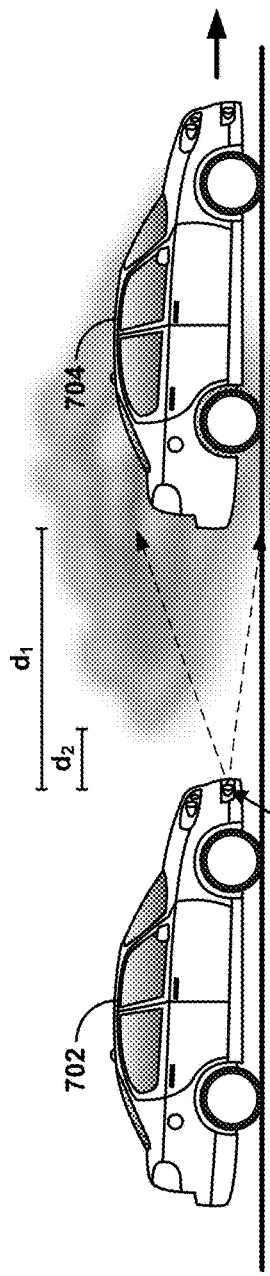
FIG. 7
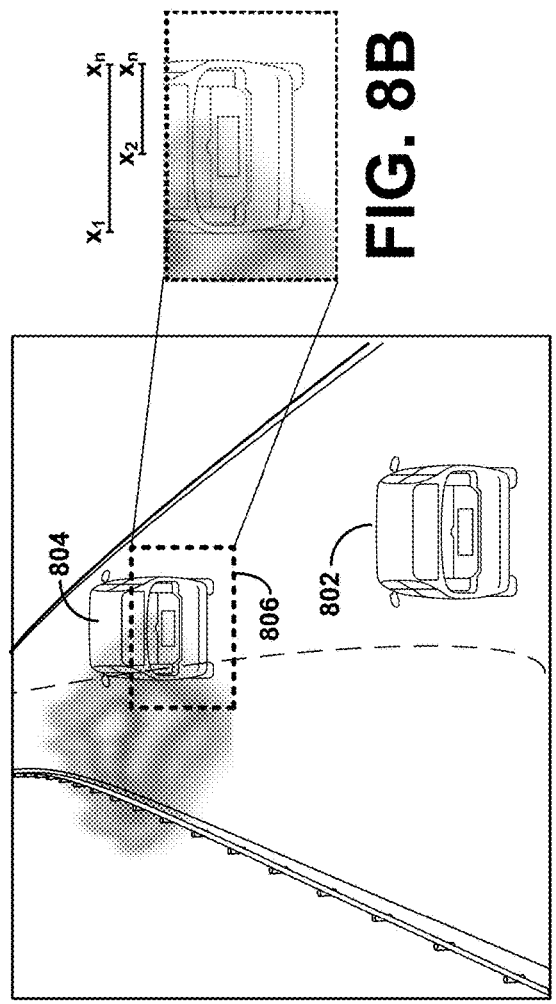
FIG. 8B
FIG. 8A

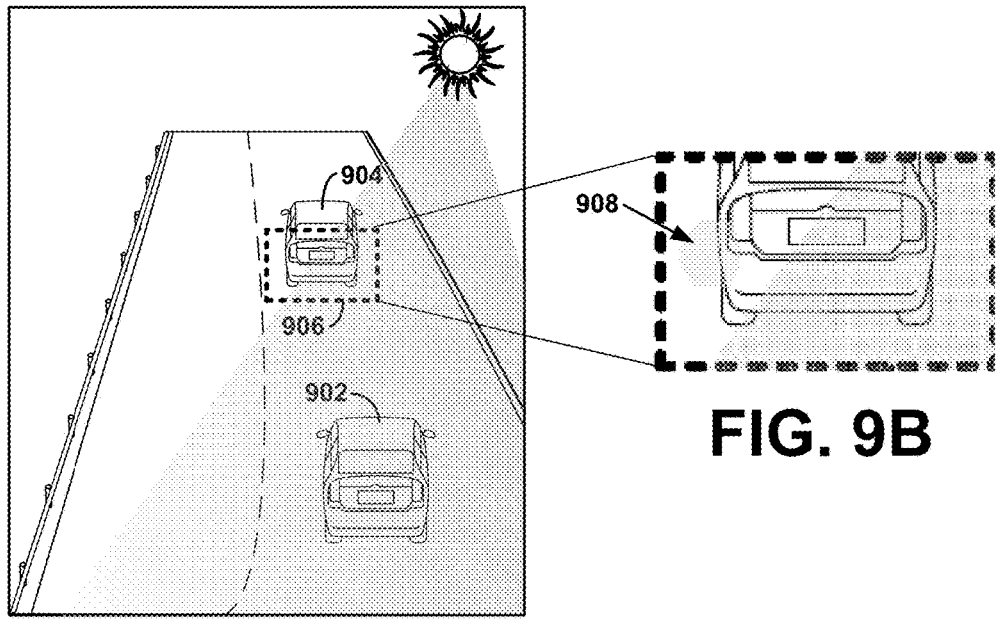
FIG. 9A
FIG. 9B
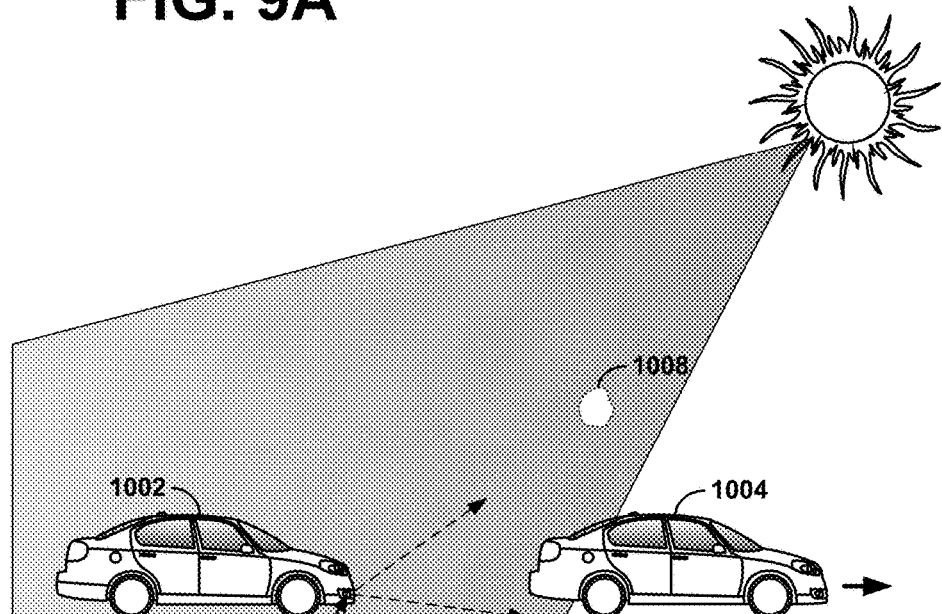
FIG. 10

METHODS AND SYSTEMS FOR DETECTING WEATHER CONDITIONS USING VEHICLE ONBOARD SENSORS

CROSS-REFERENCE TO RELATED APPLICATIONS

The present application is a continuation of U.S. patent application Ser. No. 13/888,634, filed on May 7, 2013, the entire contents of which are herein incorporated by reference.

BACKGROUND

Unless otherwise indicated herein, the materials described in this section are not prior art to the claims in this application and are not admitted to be prior art by inclusion in this section.

Autonomous vehicles use various computing systems to aid in the transport of passengers from one location to another. Some autonomous vehicles may require an initial input or continuous input from an operator, such as a pilot, driver, or passenger. Other autonomous systems, for example autopilot systems, may be used when the system has been engaged, which permits the operator to switch from a manual mode (where the operator exercises a high degree of control over the movement of the vehicle) to an autonomous mode (where the vehicle essentially drives itself) to modes that lie somewhere in between.

Such vehicles are typically equipped with various types of sensors in order to detect objects in the surroundings. For example, an autonomous vehicle may include lasers, sonar, radar, cameras, and other devices which scan and record data from surroundings of the vehicle. Sensor data from one or more of these devices may be used to detect objects and their respective characteristics (position, shape, heading, speed, etc.). This detection and identification is useful for the safe operation of autonomous vehicle.

SUMMARY

Within examples, devices and methods for detecting weather conditions using vehicle onboard sensors are provided.

In one example, a method is provided that comprises receiving laser data collected for an environment of a vehicle, and the laser data includes a plurality of laser data points. The method also comprises associating, by a computing device, laser data points of the plurality of laser data points with one or more objects in the environment. The method also comprises determining given laser data points of the plurality of laser data points that are unassociated with the one or more objects in the environment as being representative of an untracked object, and based on one or more untracked objects being determined, identifying by the computing device an indication of a weather condition of the environment.

In another example, a non-transitory computer readable storage medium having stored therein instructions, that when executed by a computing device, cause the computing device to perform functions. The functions comprise receiving laser data collected for an environment of a vehicle, and the laser data includes a plurality of laser data points. The functions also comprise associating laser data points of the plurality of laser data points with one or more objects in the environment, and determining given laser data points of the plurality of laser data points that are unassociated with the one or more objects in the environment as being representative of an untracked object. The functions also comprise based on one or more untracked objects being determined, identifying an indication of a weather condition of the environment.

In still another example, a system is provided that comprises at least one processor, and data storage comprising instructions executable by the at least one processor to cause the system to perform functions. The functions comprise receiving laser data collected for an environment of a vehicle and the laser data includes a plurality of laser data points, and associating laser data points of the plurality of laser data points with one or more objects in the environment. The functions also comprise determining given laser data points of the plurality of laser data points that are unassociated with the one or more objects in the environment as being representative of an untracked object, and based on one or more untracked objects being determined, identifying an indication of a weather condition of the environment.

In still another example, a device is provided comprising a means for receiving laser data collected for an environment of a vehicle, and the laser data includes a plurality of laser data points. The device also comprises means for associating laser data points of the plurality of laser data points with one or more objects in the environment. The device also comprises means for determining given laser data points of the plurality of laser data points that are unassociated with the one or more objects in the environment as being representative of an untracked object, and based on one or more untracked objects being determined, means for identifying by the computing device an indication of a weather condition of the environment.

These as well as other aspects, advantages, and alternatives, will become apparent to those of ordinary skill in the art by reading the following detailed description, with reference where appropriate to the accompanying figures.

BRIEF DESCRIPTION OF THE FIGURES

FIG. 7 is another example conceptual illustration of identifying a weather condition that includes fog.

FIG. 8A is another example conceptual illustration of identifying an indication that a weather condition of the environment includes fog.

FIG. 8B is an example conceptual illustration of an image captured by the vehicle in FIG. 8A.

FIG. 9A is another example conceptual illustration of identifying a weather condition, which in this instance, is a sunny condition based on camera images.

FIG. 9B is an example conceptual illustration of an image captured by the vehicle in FIG. 9A.

FIG. 10 includes another example conceptual side view illustration of identifying an indication that an environment of a vehicle is sunny.

DETAILED DESCRIPTION

Figure 1:
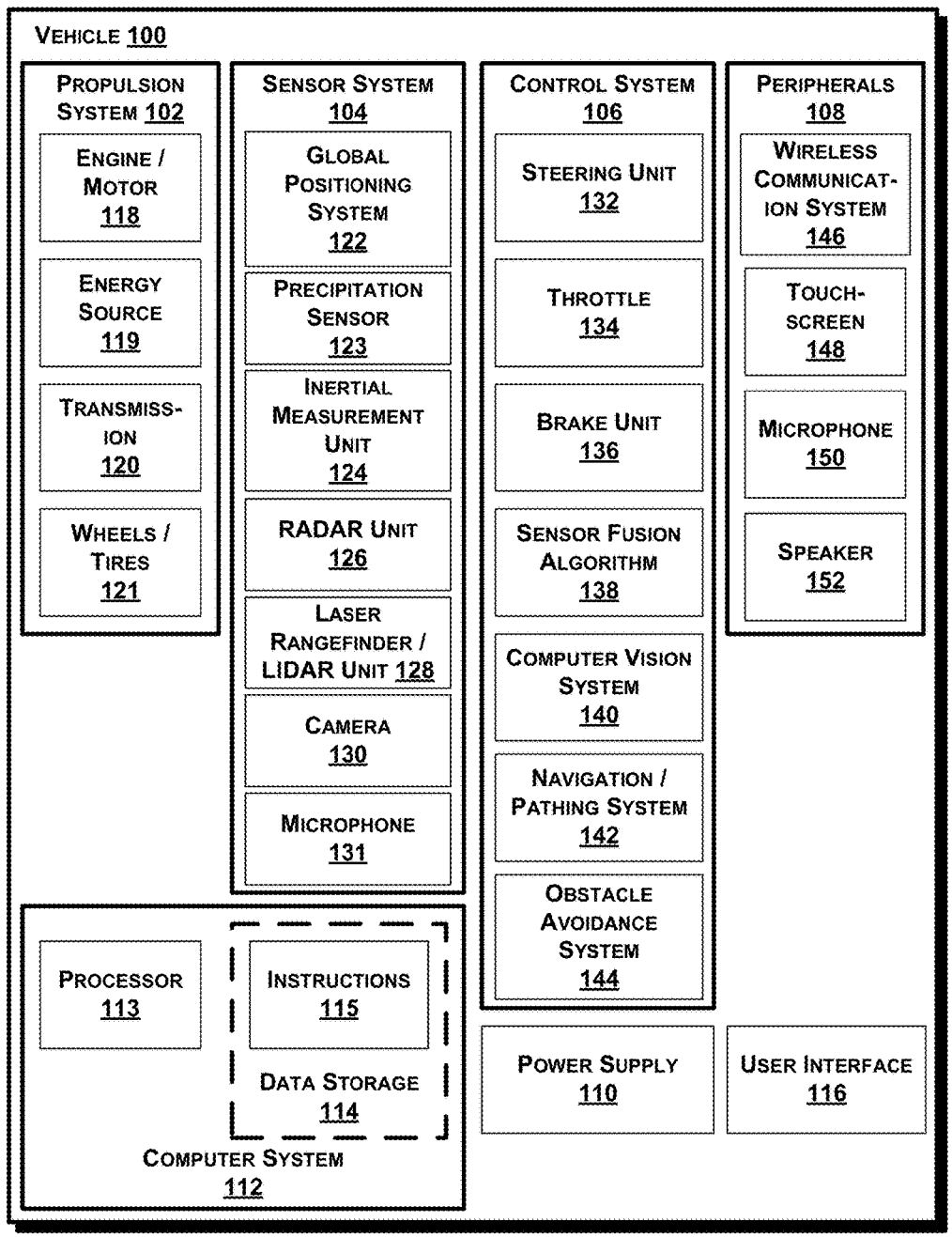
FIG. 1 is a functional block diagram depicting a vehicle according to an example embodiment.

The following detailed description describes various features and functions of the disclosed systems and methods with reference to the accompanying figures. In the figures, similar symbols identify similar components, unless context dictates otherwise, and the figures or components of the figures may not necessarily be drawn to scale for illustration purposes. The illustrative system and method embodiments described herein are not meant to be limiting. It may be readily understood that certain aspects of the disclosed systems and methods can be arranged and combined in a wide variety of different configurations, all of which are contemplated herein.

Within examples, methods and systems are provided for detecting weather conditions using vehicle onboard sensors, and modifying behavior of the vehicle accordingly. In some examples, self-driving cars or autonomous vehicles may not drive or drive as well under certain weather conditions such as heavy rain, wet-road, fog, direct sun light, etc., and thus, behavior the autonomous vehicle may be based on the detected weather condition.

In one example, a method is provided that comprises receiving laser data collected for an environment of a vehicle. A computing device may be configured to associate laser data points of the plurality of laser data points with one or more objects in the environment, and determine given laser data points of the plurality of laser data points that are unassociated with the one or more objects in the environment as being representative of an untracked object. Based on one or more untracked objects being determined, the computing device may identify an indication of a weather condition of the environment.

In a specific example, a radar sensor may be unable to detect some weather conditions, such as rain or fog (e.g., specifically rain/water that is an arch of water kicked up off of a surface by a vehicle traveling a certain speed like a rooster tail of water). However, a laser sensor may collect laser data relating to such water conditions. Thus, for any untracked received laser data (e.g., laser data that does not match to received radar data), an indication of a weather condition can be determined, and the specific weather condition can be ascertained by details of the untracked object.

As another example, sunlight may contaminate laser data by causing additional laser data points or altering wavelengths of laser data points. Thus, some laser data collected may not be representative of objects in an environment of the vehicle. By comparing to data of objects in the environment (such as tracked objects using laser or radar data), those laser data points that are contaminated may be identified, and based on identifying such contaminated data, a sunny weather condition can be made. Additional details may be accessed to further confirm the sunny weather condition, such as a geographic location of the vehicle and a time of day, information about the weather from a server, or image data from a camera coupled to the vehicle.

As yet another example, a laser sensor may be unable to detect objects through fog, and may in fact, receive data points reflected off the fog. For any untracked received laser data (e.g., laser data that does not match to tracked or known objects in the environment), an indication can be determined that the vehicle is in an environment that has a foggy weather condition.

Further information may be used to provide a higher confidence level or confirmation of the weather condition, such as a speed of the vehicle. For example, if the vehicle is not moving or moving slowly, then it is less likely that vehicles in front of the vehicle are moving fast enough to cause water to be kicked up off the road and detected by a laser sensor. Other information that may be used includes rain detector information, information about the weather from a server, or image data from a camera coupled to the sensor.

The indication of the weather condition can be useful to determine safe driving actions of an autonomous vehicle. Example actions may include providing instructions to indicate a request to transition to a manual mode, or if remaining in autonomous mode then switching to a mode specific to wet roadways (i.e., driving at slower speeds, allowing for larger distances to accomplish braking, etc.).

Example systems within the scope of the present disclosure will now be described in greater detail. Generally, an example system may be implemented in or may take the form of an automobile. However, an example system may also be implemented in or take the form of other vehicles, such as cars, trucks, motorcycles, buses, boats, airplanes, helicopters, lawn mowers, recreational vehicles, amusement park vehicles, farm equipment, construction equipment, trams, golf carts, trains, and trolleys. Other vehicles are possible as well.

FIG. 1 is a functional block diagram depicting a vehicle 100 according to an example embodiment. The vehicle 100 is configured to operate fully or partially in an autonomous mode, and thus may be referred to as an "autonomous vehicle." For example, a computer system 112 may control the vehicle 100 while in an autonomous mode via control instructions to a control system 106 for the vehicle 100. The computer system 112 may receive information from a sensor system 104, and base one or more control processes (such as the setting a heading so as to avoid a detected obstacle) upon the received information in an automated fashion.

The vehicle 100 may be fully autonomous or partially autonomous. In a partially autonomous vehicle some functions can optionally be manually controlled (e.g., by a driver) some or all of the time. Further, a partially autonomous vehicle may be configured to switch between a fully-manual operation mode and a partially-autonomous and/or a fully-autonomous operation mode.

The vehicle 100 may include various subsystems such as a propulsion system 102, a sensor system 104, a control system 106, one or more peripherals 108, as well as a power supply 110, a computer system 112, and a user interface 116. The vehicle 100 may include more or fewer subsystems and each subsystem may include multiple elements. Further, each of the subsystems and elements of vehicle 100 may be interconnected. Thus, one or more of the described functions of the vehicle 100 may be divided up into additional functional or physical components, or combined into fewer functional or physical components. In some further examples, additional functional and/or physical components may be added to the examples illustrated by FIG. 1.

The propulsion system 102 may include components operable to provide powered motion to the vehicle 100. Depending upon the embodiment, the propulsion system 102 may include an engine/motor 118, an energy source 119, a transmission 120, and wheels/tires 121. The engine/motor 118 could be any combination of an internal combustion engine, an electric motor, steam engine, Stirling engine, or other types of engines and/or motors. In some embodiments, the propulsion system 102 may include multiple types of engines and/or motors. For instance, a gas-electric hybrid vehicle may include a gasoline engine and an electric motor. Other examples are possible as well.

The energy source 119 may represent a source of energy that may, in full or in part, power the engine/motor 118. That is, the engine/motor 118 may be configured to convert the energy source 119 into mechanical energy to operate the transmission 120. Examples of energy sources 119 may include gasoline, diesel, other petroleum-based fuels, propane, other compressed gas-based fuels, ethanol, solar panels, batteries, capacitors, flywheels, regenerative braking systems, and/or other sources of electrical power, etc. The energy source 119 may also provide energy for other systems of the automobile 100.

The transmission 120 may include elements that are operable to transmit mechanical power from the engine/motor 118 to the wheels/tires 121. Such elements may include a gearbox, a clutch, a differential, a drive shaft, and/or axle(s), etc. The transmission 120 may include other elements as well. The drive shafts may include one or more axles that may be coupled to the one or more wheels/tires 121.

The wheels/tires 121 may be arranged to stably support the vehicle 100 while providing frictional traction with a surface, such as a road, upon which the vehicle 100 moves. Accordingly, the wheels/tires 121 of vehicle 100 may be configured in various formats, including a unicycle, bicycle/motorcycle, tricycle, or car/truck four-wheel format. Other wheel/tire geometries are possible, such as those including six or more wheels. Any combination of the wheels/tires 121 of vehicle 100 may be operable to rotate differentially with respect to other wheels/tires 121. The wheels/tires 121 may represent at least one wheel that is fixedly attached to the transmission 120 and at least one tire coupled to a rim of the wheel that could make contact with the driving surface. The wheels/tires 121 may include any combination of metal and rubber, or another combination of materials.

The sensor system 104 generally includes one or more sensors configured to detect information about the environment surrounding the vehicle 100. For example, the sensor system 104 may include a Global Positioning System (GPS) 122, a precipitation sensor 123, an inertial measurement unit (IMU) 124, a RADAR unit 126 (radio detection and ranging), a laser rangefinder/LIDAR unit 128 (laser imaging detection and ranging), a camera 130, and/or a microphone 131. The sensor system 104 may also include sensors configured to monitor internal systems of the vehicle 100 (e.g., $O_2$ monitor, fuel gauge, engine oil temperature, wheel speed sensors, etc.). One or more of the sensors included in the sensor system 104 may be configured to be actuated separately and/or collectively in order to modify a position and/or an orientation of the one or more sensors.

Sensors in the sensor system 104 may be configured to provide data that is processed by the computer system 112 in real-time. For example, sensors may continuously update outputs to reflect an environment being sensed at or over a range of time, and continuously or as-demanded provide that updated output to the computer system 112 so that the computer system 112 can determine whether the vehicle's then current direction or speed should be modified in response to the sensed environment.

The GPS 122 may be any sensor configured to estimate a geographic location of the vehicle 100. To this end, GPS 122 may include a transceiver operable to provide information regarding the position of the vehicle 100 with respect to the Earth.

The precipitation sensor 123 may be mounted under or incorporated into a windshield of the vehicle 100. Precipitation sensors may also be mounted at various other locations, such as at or near a location of headlamps, etc. In one example, the precipitation sensor 123 may include a set of one or more infrared light-emitting diodes (LEDs) and a photodetector such as a photodiode. Light emitted by the LEDs may be reflected by the windshield back to the photodiode. The less light the photodiode receives may be indicative of the more precipitation outside of the vehicle 100. An amount of reflected light or some other indicator of the detected amount of precipitation may be passed to computer system 112.

The IMU 124 may include any combination of sensors (e.g., accelerometers and gyroscopes) configured to sense position and orientation changes of the vehicle 100 based on inertial acceleration.

The RADAR unit 126 may represent a system that utilizes radio signals to sense objects within the local environment of the vehicle 100. In some embodiments, in addition to sensing the objects, the RADAR unit 126 may additionally be configured to sense the speed and/or heading of the objects.

Similarly, the laser rangefinder or LIDAR unit 128 may be any sensor configured to sense objects in the environment in which the vehicle 100 is located using lasers. Depending upon the embodiment, the laser rangefinder/LIDAR unit 128 could include one or more laser sources, a laser scanner, and one or more detectors, among other system components. The laser rangefinder/LIDAR unit 128 could be configured to operate in a coherent (e.g., using heterodyne detection) or an incoherent detection mode.

The camera 130 may include one or more devices configured to capture a plurality of images of the environment surrounding the vehicle 100. The camera 130 may be a still camera or a video camera. In some embodiments, the camera 130 may be mechanically movable such as by rotating and/or tilting a platform to which the camera is mounted. As such, a control process of the vehicle 100 may be implemented to control the movement of the camera 130.

The sensor system 104 may also include a microphone 131. The microphone 131 may be configured to capture sound from the environment surrounding the vehicle 100. In some cases, multiple microphones can be arranged as a microphone array, or possibly as multiple microphone arrays.

The control system 106 may be configured to control operation(s) of the vehicle 100 and its components. Accordingly, the control system 106 may include various elements include steering unit 132, throttle 134, brake unit 136, a sensor fusion algorithm 138, a computer vision system 140, a navigation/pathing system 142, and an obstacle avoidance system 144, etc.

The steering unit 132 may represent any combination of mechanisms that may be operable to adjust the heading of vehicle 100. For example, the steering unit 132 can adjust the axis (or axes) of one or more of the wheels/tires 121 so as to effect turning of the vehicle 100. The throttle 134 may be configured to control, for instance, the operating speed of the engine/motor 118 and, in turn, control the speed of the vehicle 100. The brake unit 136 may include any combination of mechanisms configured to decelerate the vehicle 100.

The brake unit 136 may, for example, use friction to slow the wheels/tires 121. In other embodiments, the brake unit 136 inductively decelerates the wheels/tires 121 by a regenerative braking process to convert kinetic energy of the wheels/tires 121 to electric current. The brake unit 136 may take other forms as well.

The sensor fusion algorithm 138 may be an algorithm (or a computer program product storing an algorithm) configured to accept data from the sensor system 104 as an input. The data may include, for example, data representing information sensed at the sensors of the sensor system 104. The sensor fusion algorithm 138 may include or be configured to be executed using, for instance, a Kalman filter, Bayesian network, or other algorithm. The sensor fusion algorithm 138 may provide various assessments based on the data from sensor system 104. Depending upon the embodiment, the assessments may include evaluations of individual objects and/or features in the environment of vehicle 100, evaluations of particular situations, and/or evaluations of possible impacts based on the particular situation. Other assessments are possible.

The computer vision system 140 may be any system operable to process and analyze images captured by camera 130 in order to identify objects and/or features in the environment of vehicle 100 that could include traffic signals, road way boundaries, other vehicles, pedestrians, and/or obstacles, etc. The computer vision system 140 may use an object recognition algorithm, a Structure From Motion (SFM) algorithm, video tracking, and other computer vision techniques. In some embodiments, the computer vision system 140 could be additionally configured to map an environment, track objects, estimate the speed of objects, etc.

The navigation and pathing system 142 may be any system configured to determine a driving path for the vehicle 100. For example, the navigation/pathing system 142 may determine a series of speeds and directional headings to effect movement of the vehicle 100 along a path that substantially avoids perceived obstacles while generally advancing the vehicle 100 along a roadway-based path leading to an ultimate destination, which may be set according to user inputs via the user interface 116, for example. The navigation and pathing system 142 may additionally be configured to update the driving path dynamically while the vehicle 100 is in operation. In some embodiments, the navigation and pathing system 142 could be configured to incorporate data from the sensor fusion algorithm 138, the GPS 122, and one or more predetermined maps so as to determine the driving path for vehicle 100.

The obstacle avoidance system 144 may represent a control system configured to identify, evaluate, and avoid or otherwise negotiate potential obstacles in the environment of the vehicle 100. For example, the obstacle avoidance system 144 may effect changes in the navigation of the vehicle 100 by operating one or more subsystems in the control system 106 to undertake swerving maneuvers, turning maneuvers, braking maneuvers, etc. In some embodiments, the obstacle avoidance system 144 is configured to automatically determine feasible ("available") obstacle avoidance maneuvers on the basis of surrounding traffic patterns, road conditions, etc. For example, the obstacle avoidance system 144 may be configured such that a swerving maneuver is not undertaken when other sensor systems detect vehicles, construction barriers, other obstacles, etc. in the region adjacent the vehicle 100 that would be swerved into. In some embodiments, the obstacle avoidance system 144 may automatically select the maneuver that is both available and maximizes safety of occupants of the vehicle. For example, the obstacle avoidance system 144 may select an avoidance maneuver predicted to cause the least amount of acceleration in a passenger cabin of the vehicle 100.

The control system 106 may additionally or alternatively include components other than those shown and described.

The vehicle 100 also includes peripherals 108 configured to allow interaction between the vehicle 100 and external sensors, other vehicles, other computer systems, and/or a user, such as an occupant of the vehicle 100. For example, the peripherals 108 for receiving information from occupants, external systems, etc. may include a wireless communication system 146, a touchscreen 148, a microphone 150, and/or a speaker 152.

In some embodiments, the peripherals 108 function to receive inputs for a user of the vehicle 100 to interact with the user interface 116. To this end, the touchscreen 148 can both provide information to a user of the vehicle 100, and convey information from the user indicated via the touchscreen 148 to the user interface 116. The touchscreen 148 can be configured to sense both touch positions and touch gestures from the finger of a user (or stylus, etc.) via capacitive sensing, resistance sensing, optical sensing, a surface acoustic wave process, etc. The touchscreen 148 can be capable of sensing finger movement in a direction parallel or planar to the touchscreen surface, in a direction normal to the touchscreen surface, or both, and may also be capable of sensing a level of pressure applied to the touchscreen surface. An occupant of the vehicle 100 can also utilize a voice command interface. For example, the microphone 150 can be configured to receive audio (e.g., a voice command or other audio input) from an occupant of the vehicle 100. Similarly, the speaker 152 can be configured to output audio to the occupant of the vehicle 100.

In some embodiments, the peripherals 108 function to allow communication between the vehicle 100 and external systems, such as devices, sensors, other vehicles, etc. within its surrounding environment and/or controllers, servers, etc., physically located far from the vehicle 100 that provide useful information regarding the vehicle's surroundings, such as traffic information, weather information, etc. For example, the wireless communication system 146 can wirelessly communicate with one or more devices directly or via a communication network. The wireless communication system 146 can optionally use 3G cellular communication, such as CDMA, EVDO, GSM/GPRS, and/or 4G cellular communication, such as WiMAX or LTE. Additionally or alternatively, the wireless communication system 146 can communicate with a wireless local area network (WLAN), for example, using WiFi. In some embodiments, the wireless communication system 146 could communicate directly with a device, for example, using an infrared link, short-range wireless link, etc. The wireless communication system 146 can include one or more dedicated short range communication (DSRC) devices that can include public and/or private data communications between vehicles and/or roadside stations. Other wireless protocols for sending and receiving information embedded in signals, such as various vehicular communication systems, can also be employed by the wireless communication system 146 within the context of the present disclosure.

The power supply 110 may provide power to components of the vehicle 100, such as electronics in the peripherals 108, the computer system 112, the sensor system 104, etc. The power supply 110 can include a rechargeable lithium-ion or lead-acid battery for storing and discharging electrical energy to the various powered components, for example. In some embodiments, one or more banks of batteries may be configured to provide electrical power. In some embodiments, the power supply 110 and the energy source 119 can be implemented together, as in some all-electric cars.

Many or all of the functions of the vehicle 100 may be controlled via the computer system 112 that receives inputs from the sensor system 104, the peripherals 108, etc., and communicates appropriate control signals to the propulsion system 102, the control system 106, the peripherals 108, etc. to effect automatic operation of the vehicle 100 based on its surroundings. The computer system 112 may include at least one processor 113 (which could include at least one microprocessor) that executes instructions 115 stored in a non-transitory computer readable medium, such as the data storage 114. The computer system 112 may also represent a plurality of computing devices that may serve to control individual components or subsystems of the vehicle 100 in a distributed fashion.

In some embodiments, data storage 114 may contain instructions 115 (e.g., program logic) executable by the processor 113 to execute various automobile functions, including those described above in connection with FIG. 1. Data storage 114 may contain additional instructions as well, including instructions to transmit data to, receive data from, interact with, and/or control one or more of the propulsion system 102, the sensor system 104, the control system 106, and the peripherals 108.

In addition to the instructions 115, the data storage 114 may store data such as roadway maps, path information, among other information. Such information may be used by vehicle 100 and computer system 112 at during the operation of the vehicle 100 in the autonomous, semi-autonomous, and/or manual modes.

The vehicle 100, and associated computer system 112, provides information to and/or receives input from, a user of the vehicle 100, such as an occupant in a passenger cabin of the vehicle 100. Accordingly, the vehicle 100 may include a user interface 116 for providing information to or receiving input from a user of vehicle 100. The user interface 116 may control or enable control of content and/or the layout of interactive images that could be displayed on the touchscreen 148. Further, the user interface 116 could include one or more input/output devices within the set of peripherals 108, such as the wireless communication system 146, the touchscreen 148, the microphone 150, and the speaker 152.

The computer system 112 controls the operation of the vehicle 100 based on inputs received from various subsystems indicating vehicle and/or environmental conditions (e.g., propulsion system 102, sensor system 104, and/or control system 106), as well as inputs from the user interface 116, indicating user preferences. For example, the computer system 112 may utilize input from the control system 106 to control the steering unit 132 to avoid an obstacle detected by the sensor system 104 and the obstacle avoidance system 144. The computer system 112 may be configured to control many aspects of the vehicle 100 and its subsystems. Generally, however, provisions are made for manually overriding automated controller-driven operation, such as in the event of an emergency, or merely in response to a user-activated override, etc.

The components of the vehicle 100 described herein may be configured to work in an interconnected fashion with other components within or outside their respective systems. For example, the camera 130 can capture a plurality of images that represent information about an environment of the vehicle 100 while operating in an autonomous mode. The environment may include other vehicles, traffic lights, traffic signs, road markers, pedestrians, etc. The computer vision system 140 can categorize and/or recognize various aspects in the environment in concert with the sensor fusion algorithm 138, the computer system 112, etc. based on object recognition models pre-stored in the data storage 114, and/or by other techniques.

Although FIG. 1 shows various components of vehicle 100, i.e., wireless communication system 146, computer system 112, data storage 114, and user interface 116, as being integrated into the vehicle 100, one or more of these components could be mounted or associated separately from the vehicle 100. For example, data storage 114 could, in part or in full, exist separate from the vehicle 100. Thus, the vehicle 100 could be provided in the form of device elements that may be located separately or together. The device elements that make up vehicle 100 may generally be communicatively coupled together in a wired and/or wireless fashion.

Figure 2:
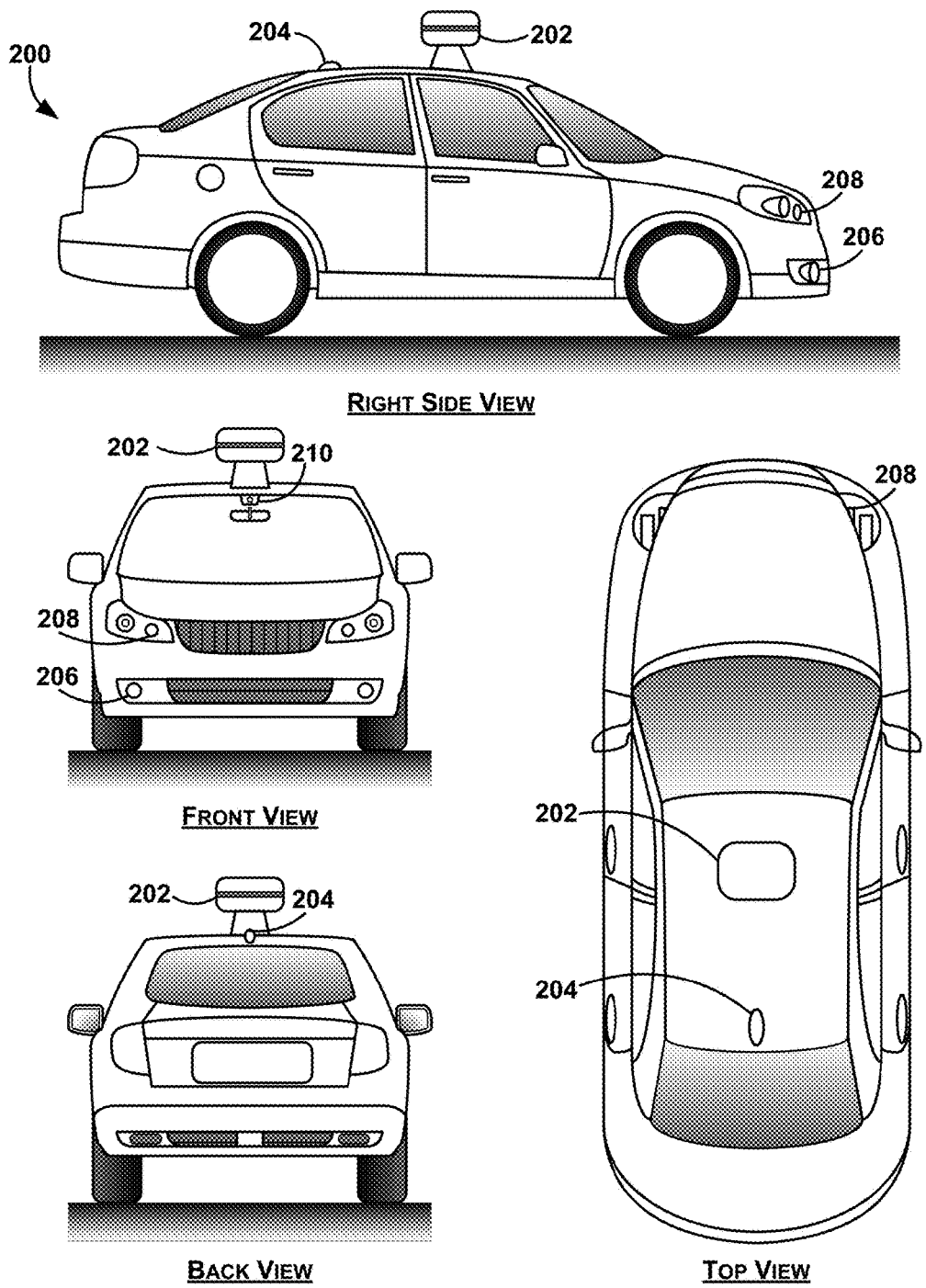
FIG. 2 depicts an example vehicle that can include all or some of the functions described in connection with the vehicle in reference to FIG. 1.

FIG. 2 depicts an example vehicle 200 that can include all or some of the functions described in connection with the vehicle 100 in reference to FIG. 1. Although example vehicle 200 is illustrated in FIG. 2 as a four-wheel sedan-type car for illustrative purposes, the present disclosure is not so limited. For instance, example vehicle 200 can represent any type of vehicle.

Example vehicle 200 includes a sensor unit 202, a wireless communication system 204, a LIDAR unit 206, a laser rangefinder unit 208, and a camera 210. Furthermore, example vehicle 200 may include any of the components described in connection with vehicle 100 of FIG. 1.

The sensor unit 202 is mounted atop example vehicle 200 and includes one or more sensors configured to detect information about an environment surrounding example vehicle 200, and output indications of the information. For example, the sensor unit 202 may include any combination of cameras, RADARs, LIDARs, range finders, and acoustic sensors. The sensor unit 202 may include one or more movable mounts that may be operable to adjust the orientation of one or more sensors in the sensor unit 202. In one embodiment, the movable mount may include a rotating platform that may scan sensors so as to obtain information from each direction around example vehicle 200. In another embodiment, the movable mount of the sensor unit 202 may be moveable in a scanning fashion within a particular range of angles and/or azimuths. The sensor unit 202 may be mounted atop the roof of a car, for instance, however other mounting locations are possible. Additionally, the sensors of the sensor unit 202 may be distributed in different locations and need not be collocated in a single location. Some possible sensor types and mounting locations include the LIDAR unit 206 and laser rangefinder unit 208. Furthermore, each sensor of the sensor unit 202 may be configured to be moved or scanned independently of other sensors of the sensor unit 202.

The wireless communication system 204 may be located on a roof of example vehicle 200 as depicted in FIG. 2. Alternatively, the wireless communication system 204 may be located, fully or in part, elsewhere. The wireless communication system 204 may include wireless transmitters and receivers that may be configured to communicate with devices external or internal to example vehicle 200. Specifically, the wireless communication system 204 may include transceivers configured to communicate with other vehicles and/or computing devices, for instance, in a vehicular communication system or a roadway station. Examples of such vehicular communication systems include dedicated short range communications (DSRC), radio frequency identification (RFID), and other proposed communication standards directed towards intelligent transport systems.

The camera 210 may be a photo-sensitive instrument, such as a still camera, a video camera, etc., that is configured to capture a plurality of images of the environment of example vehicle 200. To this end, the camera 210 can be configured to detect visible light, and can additionally or alternatively be configured to detect light from other portions of the spectrum, such as infrared or ultraviolet light. The camera 210 can be a two-dimensional detector, and can optionally have a three-dimensional spatial range of sensitivity. In some embodiments, the camera 210 can include, for example, a range detector configured to generate a two-dimensional image indicating distance from the camera 210 to a number of points in the environment. To this end, the camera 210 may use one or more range detecting techniques.

For example, the camera 210 may provide range information by using a structured light technique in which example vehicle 200 illuminates an object in the environment with a predetermined light pattern, such as a grid or checkerboard pattern and uses the camera 210 to detect a reflection of the predetermined light pattern from environmental surroundings. Based on distortions in the reflected light pattern, example vehicle 200 may determine the distance to the points on the object. The predetermined light pattern may comprise infrared light, or radiation at other suitable wavelengths for such measurements.

The camera 210 may be mounted inside a front windshield of example vehicle 200. Specifically, the camera 210 may be situated to capture images from a forward-looking view with respect to the orientation of example vehicle 200. Other mounting locations and viewing angles of the camera 210 may also be used, either inside or outside example vehicle 200.

The camera 210 can have associated optics operable to provide an adjustable field of view. Further, the camera 210 may be mounted to example vehicle 200 with a movable mount to vary a pointing angle of the camera 210, such as a via a pan/tilt mechanism.

Figure 3:
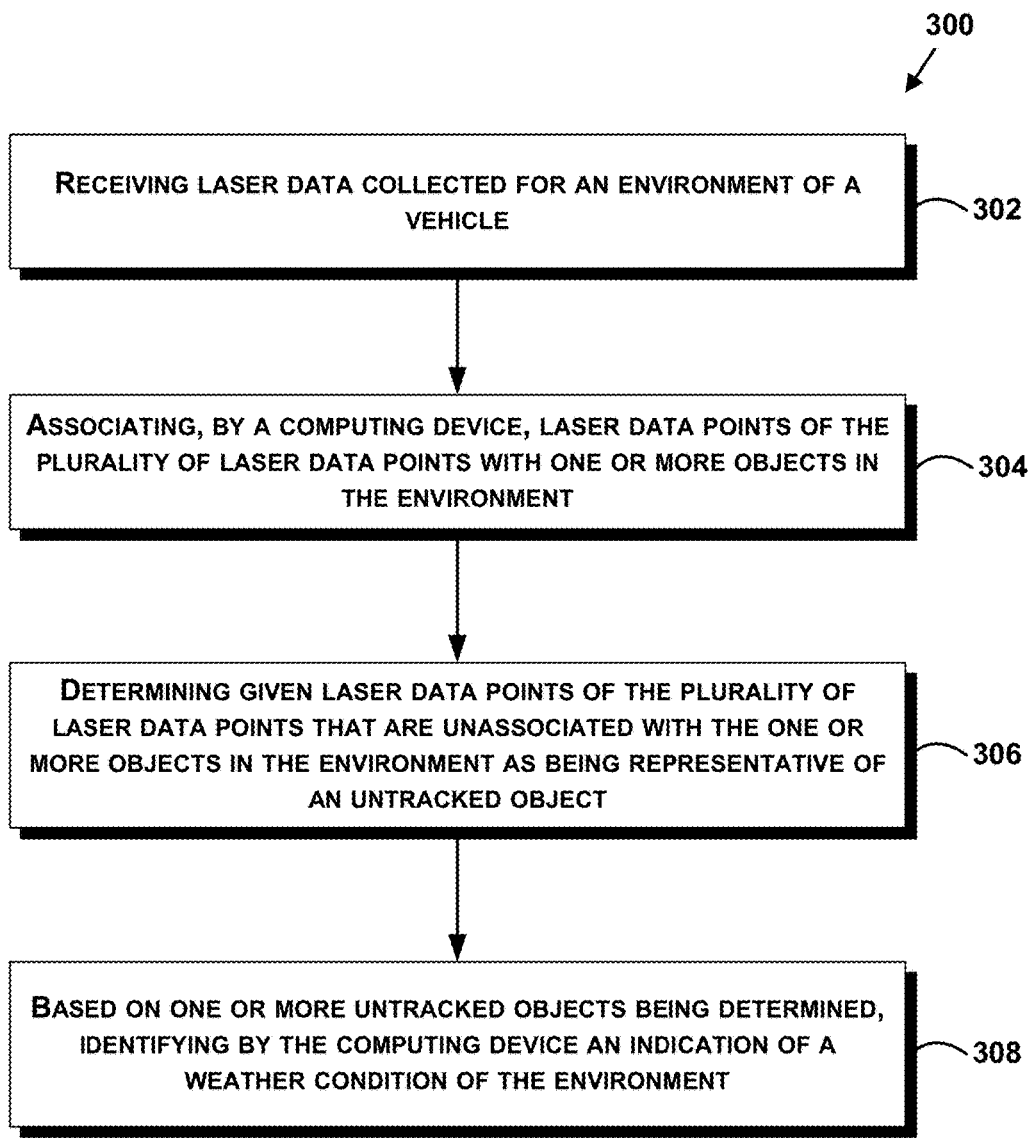
FIG. 3 is a block diagram of an example method for detecting a weather condition using onboard vehicle sensors, in accordance with at least some embodiments described herein.

FIG. 3 is a block diagram of an example method for detecting a weather condition using onboard vehicle sensors, in accordance with at least some embodiments described herein. Method 300 shown in FIG. 3 presents an embodiment of a method that, for example, could be used with the vehicle 100 and/or vehicle 200 as illustrated and described in reference to FIGS. 1 and 2, respectively, or components of the vehicle 100 or vehicle 200. For example, the processes described herein may be carried out by the RADAR unit 126, the LIDAR unit 128, or camera 130 mounted to an autonomous vehicle (e.g., vehicle 200) in communication with the computer system 112, the sensor fusion algorithm 138, and/or the computer vision system 140. Method 300 may include one or more operations, functions, or actions as illustrated by one or more of blocks 302-308. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation.

In addition, for the method 300 and other processes and methods disclosed herein, the flowchart shows functionality and operation of one possible implementation of present embodiments. In this regard, each block may represent a module, a segment, or a portion of program code, which includes one or more instructions (e.g., machine readable code) executable by a processor for implementing specific logical functions or steps in the process. The program code may be stored on any type of computer readable medium, for example, such as a storage device including a disk or hard drive. The computer readable medium may include a non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, a tangible storage device, a computer program product, or other article of manufacture, for example.

The non-transitory computer readable medium could also be distributed among multiple data storage elements, which could be remotely located from each other. A computing device that executes some or all of the stored instructions could be a vehicle, such as the example vehicle 200 illustrated in FIG. 2. Alternatively, the computing device that executes some or all of the stored instructions could be another computing device, such as a server.

In addition, for the method 300 and other processes and methods disclosed herein, each block in FIG. 3 may represent circuitry that is wired to perform the specific logical functions in the process.

Example methods, such as method 300 of FIG. 3 may be carried out in whole or in part by the vehicle and its subsystems. Accordingly, example methods could be described by way of example herein as being implemented by the vehicle. However, it should be understood that an example method may be implemented in whole or in part by other computing devices of the vehicle or separate from the vehicle. For example, an example method may be implemented in whole or in part by a server system, which receives data from a device such as those associated with the vehicle. Other examples of computing devices or combinations of computing devices that can implement an example method are possible.

At block 302, the method 300 includes receiving laser data collected for an environment of a vehicle. The laser data includes a plurality of laser data points that are based on objects in the environment that are perceived to be physically present due to reflected or backscattered light. The vehicle, or components of the vehicle such as a computing device or processor, may be configured to receive laser data that is collected.

As an example, the vehicle may have a LIDAR unit that illuminates areas around, surrounding, in front of, behind, to the side, or in any proximity or relation to the vehicle, and detects reflected light. In operation, the LIDAR rotates and (e.g., periodically) emits laser beams. Reflections from the emitted laser beams by objects in the environment are then received by suitable sensors. Time-stamping receipt of the reflected signals allows for associating each reflected signal (if any is received at all) with the most recently emitted laser pulse, and measuring the time delay between emission of the laser pulse and reception of the reflected light. The time delay provides an estimate of the distance to the reflective feature by scaling according to the speed of light in the intervening atmosphere. Combining the distance information for each reflected signal with the orientation of the LIDAR device for the respective pulse emission allows for determining a position of the reflective feature in three-dimensions. For illustrative purposes, an environmental scene can be described in the two-dimensional x-y plane in connection with a single sweep of the LIDAR device that estimates positions to a series of points located in the x-y plane. However, it is noted that a more complete three-dimensional sampling is provided by either adjusting beam steering optics to direct the laser beam up or down from the x-y plane on its next sweep of the scene or by providing additional lasers and associated beam steering optics dedicated to sampling point locations in planes above and below the x-y plane, or combinations of these.

At block 304, the method 300 includes associating, by a computing device, laser data points of the plurality of laser data points with one or more objects in the environment. As an example, a tracking system may be used to track objects, and laser data points that are associated with tracked objects can be determined.

In some examples, a point cloud corresponding to objects in the environmental can be generated. Each point in the point cloud can be referenced by an azimuth angle (e.g., orientation of the LIDAR device while emitting the pulse corresponding to the point, which is determined by the orientation of an rotating angled mirror of the LIDAR) and a line-of-sight (LOS) distance (e.g., a distance indicated by the time delay between pulse emission and reflected light reception). For pulses that do not result in a returning reflected signal, the distance in the point map can optionally be set to the maximum distance sensitivity of the LIDAR device. The maximum distance sensitivity can be determined according to the maximum time delay the associated optical sensors wait for a return reflected signal following each pulse emission, which can itself be set according to the anticipated signal strength of a reflected signal at a particular distance given ambient lighting conditions, intensity of the emitted pulse, predicted reflectivity of environmental features, etc. In some examples, the maximum distance can be approximately 60 meters, 80 meters, 100 meters, or 150 meters, but other examples are possible for particular configurations of the LIDAR device and associated optical sensors.

In some embodiments, the sensor fusion algorithm 138, computer vision system 140, and/or computer system 112 illustrated in FIG. 1, can be configured to interpret the collected laser data alone and/or in combination with additional sensor-indicated information and/or memory-based pattern-matching point clouds and/or baseline maps of the environment to categorize or identify group of points as corresponding to objects in the environment.

Further, each spatial point can be associated with a respective laser from a set of lasers and a respective timestamp. That is, in an embodiment where the LIDAR includes multiple lasers, each respective received spatial point can be associated with the particular laser that was detected in accordance with the respective received spatial point. Additionally, each respective spatial point can be associated with a respective timestamp (e.g., a time at which laser was emitted or received). In this way, the received spatial points may be organized, identified, or otherwise ordered on a spatial (laser identification) and/or temporal (timestamp) basis. Such an ordering may assist or improve an analysis of the spatial-point data by allowing for organizing the spatial-point data into a meaningful order.

In some examples, object detection is provided in connection with an example LIDAR device. The LIDAR device may be configured to capture laser point cloud images using one or more lasers. The laser point cloud includes many points for each pulse emitted from the LIDAR device; reflected signals may indicate actual locations of reflective objects, whereas failing to receive reflected signals indicate an absence of sufficiently reflective objects within a particular distance along the line of sight of the laser. Depending on factors including the laser pulse rate, the scene refresh rate, the total solid angle sampled by each LIDAR device (or just the total solid angle of the scene, where only one LIDAR device is used), the number of sample points in each point cloud can be determined. Some embodiments can provide point clouds with as many as 50,000 laser-indicated points, 80,000 laser-indicated points, 100,000 laser-indicated points, etc. Generally, the number of laser-indicated points in each point cloud is a tradeoff between angular resolution on the one hand, and refresh rate on the other hand. The LIDAR device is driven to provide an angular resolution at a sufficiently high refresh rate to be relevant to real time navigational decisions for an autonomous vehicle. Thus, the LIDAR device can be configured to capture one or more laser point clouds of the scanning zone at predetermined time intervals, such as 100 milliseconds (to achieve a refresh rate of 10 frames per second), 33 milliseconds (to achieve a refresh rate of 30 frames per second), 1 millisecond, 1 second, etc.

With reference to FIG. 1, data storage 114 of computer system 112 of vehicle 100 can store object-detector software, code, or other program instructions. Such object-detector software can include, or be part of, one or more of the control systems 106 described above, including the sensor fusion algorithm 138, computer vision system 140, and/or obstacle avoidance system 144. The object detector may be any configuration of software and/or hardware configured to perceive features in the environmental scene by categorizing and/or identifying objects based on the laser point clouds captured by the LIDAR 128 and/or based on one or more of the sensors in sensor system 104. As a laser point cloud is captured via LIDAR 128, data indicative of the captured point cloud is communicated to the object detector, which analyzes the data to determine whether there is an object present in the laser point cloud. Objects indicated by the point cloud may be, for example, a vehicle, a pedestrian, a road sign, a traffic light, a traffic cone, etc.

To determine whether an object is present in a laser point cloud image (based on received laser data), the object detector software and/or module can associate arrangements of laser-indicated points with patterns matching objects, environmental features, and/or categories of objects or features. The object detector can be pre-loaded (or dynamically instructed) to associate arrangements according to one or more parameters corresponding to physical objects/features in the environment surrounding the vehicle 100. For example, the object detector can be pre-loaded with information indicating a typical height of a pedestrian, a length of a typical automobile, confidence thresholds for classifying suspected objects, etc.

When the object detector identifies an object in point cloud, the object detector can define a bounding box encompassing that object. For example, the bounding box can correspond to a predicted exterior surface of the point cloud indicated object. Of course, the bounding "box" can generally take the form of a multi-sided closed shape defining the predicted outer boundaries of the object.

For each captured point cloud, positions of perceived objects and their corresponding boundary definitions are associated with a frame number or frame time. Thus, similarly shaped objects appearing in roughly similar locations in successive scans of the scene can be associated with one another to track objects in time. For perceived objects appearing in multiple point cloud frames (e.g., complete scans of the scanning zone), the object can be associated, for each frame on which the object appears, with a distinct bounding shape defining the dimensional extent of the perceived object.

Perceived objects can be tracked as the vehicle 100 travels through its surrounding environment and/or as objects move with respect to the vehicle so as to pass through the scanning zone of the LIDAR device 128. Combining two or more successively captured point clouds can thereby allow for determining translation information for detected objects. Future position predictions can be made for objects with characterized motion profiles, such as by observing acceleration and/or velocity of objects such as cars moving along the roadway with the vehicle 100 to predict the location of the object during a subsequent scan. In some embodiments, objects moving through the air are assumed to move along a trajectory influenced by the force of gravity.

To assist in providing object recognition, the vehicle 100 can also be in communication with an object-identification server (e.g., via the wireless communication system 146). The object-identification server can verify and/or classify objects detected by vehicle 100 using the object detector. Moreover, the object-identification server can facilitate optimization of one or more of the parameters used by the object detector to detect objects in the captured laser point cloud based on accumulated data from other similar systems, local conditions. In one embodiment, vehicle 100 can communicate the object boundaries, and their corresponding object parameters, to the object identification server for verification that the perceived objects are correctly identified, such as indicated by an evaluation for statistical likelihood of correct identification.

Referring back to FIG. 3, at block 306, the method includes determining given laser data points of the plurality of laser data points that are unassociated with the one or more objects in the environment as being representative of an untracked object. Within examples, for laser data that is deemed to be representative of an object, the laser data may be associated with the object in the environment, and remaining received or collected laser data may be considered unassociated with the objects in the environment.

Within examples, the method 300 may be executed to determine instances in which objects are not detected by the laser that are expected to be present or objects are detected that are unexpected (i.e., laser measurements are lost or altered due to the fog). As described above, for received reflected laser data, it may be determined that an object is present to cause the laser to be reflected. But, in certain weather conditions, such as foggy conditions, the fog may cause a reflection, resulting in a false determination of an object. To determine when laser data is based on real objects present in an environment versus a weather related condition that causes a reflection of laser emissions, the computing device can be configured to compare laser data with laser data known to be representative of objects and/or known to be due to weather related reflections. Thus, comparison of received laser data with patterns of laser data known to be representative of objects can be made to identify laser data likely to be due to something other than an object.

Any number of patterns of laser data may be stored and referenced for comparison to the unassociated laser data to categorize the unassociated laser data as being representative of an object or due to a weather condition, such as fog.

As another example to distinguish between laser data due to objects and due to other conditions (e.g., a fog), the computing device may be configured to track movement of objects as represented by laser data. Thus, all laser data may be tracked as being representative of moving objects, and objects that are seen to move in an odd manner, or that appear and disappear over a short time frame, may be considered false objects that are due to laser data reflections caused by a weather condition.

In some examples, laser data collected for the environment of the vehicle comprises can be collected by performing scans of the environment over time as the vehicle travels. Objects in the environment can be tracked, based on objects determined to be present due to received laser data, as the vehicle moves through the environment. Laser data that does not match to tracked objects can then be identified.

In one example, laser data may relate to presence of water in the air or cloudy conditions typical with a fog, and such water droplets or clouds are untracked items by the vehicle's tracking system. For example, to a LIDAR device, which detects and locates optically reflective features, water droplets in the air or cloud features in the air resemble an object cloud because light pulses are reflected from the particulates. The LIDAR device may not be able to penetrate through a fog, and thus, when a fog is present, many laser points may be returned due to the fog. Thus, for any untracked received laser data (e.g., laser data that does not match to tracked objects), untracked objects can be determined.

Within examples, the method 300 may include determining the laser data points that are unassociated with the one or more objects in the environment. The LIDAR may be configured to perform a first scan of the environment, and associating the laser data points of the plurality of laser data points with one or more objects in the environment. The LIDAR may then be configured to perform a second scan of the environment, and determine laser data points that match to the one or more objects based on a location of an object represented by the laser data points. Then, laser data points of the second scan that are unassociated with the one or more objects in the environment based on a lack of a match to the one or more objects in the first scan can be determined. In further examples, the second scan may be representative of a scan of the environment after the first scan or after a number of scans so that object tracking has occurred over some time for comparison to the second scan data.

At block 308, the method 300 includes based on one or more untracked objects being determined, identifying by the computing device an indication of a weather condition of the environment. In some examples, the identification may be based on determining that a number of untracked objects are present.

In addition (or alternatively), at block 306, the method 300 may include determining that a number of laser data points that are unassociated with the one or more objects in the environment exceeds a predefined threshold, and then identifying by the computing device an indication of the weather condition. For instance, if there are a few laser data points unassociated with objects, this may be due to any number of factors; however, for a certain threshold number of laser data points, a higher probably may exist that these are due to emitted laser beams reflected off of water, due to sunlight, due to fog, or due to some other weather condition.

The method 300 may further include determining the specific weather condition. As an example, to determine a sunny weather condition, the method may include determining that the untracked object remains at a substantially same relative position with respect to the vehicle as the vehicle moves. In one example, coordinate positions of the untracked object can be determined over time, and a distance to the vehicle can be determined as well as an angle with respect to the vehicle. As the vehicle moves, objects that stay at the same distance to the vehicle would be considered to move as well. In addition, as the vehicle moves, objects that remain at a same angle with respect to the vehicle would be considered to move too. However, when an angle of the object is above 45 degrees or more, the object may be considered to be due to a sunlight reflection. In other examples, objects that are deemed to move substantially the same as the vehicle may be determined to be due to sunlight, which remains substantially constant during sunny weather conditions.

Thus, in further examples, a position of objects represented by the laser data can be determined, and based on the objects being at or within predetermined positions, a specific weather condition can be determined that the environment of the vehicle is sunny. For example, when the laser data is representative of objects or obstacles suspended at a certain height or angle with respect to the vehicle, such as at a 45 degree angle and at 5-20 feet above the vehicle, and such objects are continued to be represented by the laser data collected over time, the computing device may make a determination that the laser data does not represent a real object or obstacle. Rather, the laser data may be due to spurious observations or laser returns received from the sun that is at a fixed position relative to the vehicle. Thus, based on laser data being representative of objects in areas not expected, this may be an additional factor to consider when identifying that the environment is sunny.

In still further examples, with an autonomous vehicle or other vehicle, a time of day and a geographic location (e.g., using GPS) can be determined, and using this information, an approximate location of the sun can be determined. Based on the location of the sun relative to the vehicle, laser data representative of objects within a predetermined area can be identified as being due to reflections or rays from the sun. For example, laser data representative of objects that are substantially directed toward the approximate position of the sun, such as objects at a 45 degree angle with respect to the vehicle, may be determined to be false objects.

For example, a LIDAR device uses a laser to illuminate a target and then analyzes a reflection, and sunlight reflection off a reflective target may saturate the LIDAR device or produce an invalid or less accurate reading. To a LIDAR device, which detects and locates optically reflective features, laser artifacts due to direct sun light may be generated. Sunlight may overlap with laser wavelengths, and the LIDAR device may receive sunlight and interpret the sunlight as a returned laser creating an artifact. Thus, for any untracked received laser data (e.g., laser data that does not match to tracked objects), an indication can be determined that a weather condition of the environment of the vehicle is sunny.

In further examples, intensity values of laser data may be used to determine specific weather conditions. As a vehicle's laser or lasers are moved along, the vehicle may collect data points including range and intensity information for the same location (point or area) from several directions and/or at different times. For example, each data point may include an intensity value indicative of reflectivity of an object from which light was received by the laser as well as location information. Highly reflective surfaces, such as lane markers, may be associated with an intensity value which is greater than less reflective surfaces, such as blacktop, cement, or other roadway surfaces. Similarly, darker objects (black, navy blue, brown, etc.) which absorb more light may be associated with a lower intensity value than lighter colored objects which may reflect more light (white, cream, silver, etc.). In this regard, when an object is wet, it may become darker and therefore, rather than increasing the intensity value of an object, the water may decrease the intensity value.

In some examples, intensity values of laser data point may be scaled, for example, from 0-250, where 0 is dark and 250 is bright. Thus, more reflective, brighter surfaces may be associated with intensity values closer to 250, while less reflective, darker surfaces may be associated with intensity values closer to 0. A laser scan data may be received and processed to generate geographic location coordinates. These geographic location coordinates may include GPS latitude and longitude coordinates (x,y) with an elevation component (z), or may be associated with other coordinate systems. A result of this processing is a set of data point. Each data point of this set may include an intensity value indicative of reflectivity of the object from which the light was received by the laser as well as location information: (x,y,z).

An average intensity of the laser data points for a roadway may be compared to a threshold to further identify an indication of whether the roadway is wet. For example, as noted above, the water covering wet or icy areas of the roadway may decrease the intensity of laser data collected on the roadway. Thus, a wet roadway may have laser data with average intensity values that are somewhat lower that of dry roadways (such as cement, blacktop, brick, etc.) as well as other expected roadway features such as lane markers, etc. that appear in the map information. If some percentage of the examined laser data points have intensity values below a certain threshold value, a determination that the roadway is wet can be made. For example, using the 0 to 250 scale described above, if there are 1000 laser data points in the roadway and at least 850 of these 1000 points (or at least 85% of these laser data points) have an intensity below a threshold of 10, the roadway is dark. As noted above, a lower intensity value may indicate a high probability that the roadway is wet. Other thresholds and percentages may also be used, for example, based on the expected intensity or the composition of the roadway.

In further examples, the method 300 may include determining a location of the vehicle, determining a distribution of expected values of laser data for the surface on which the vehicle travels for certain weather conditions based on the location of the vehicle, and comparing the determined distribution to the laser data collected for the environment of the vehicle. The distribution of expected values of laser data for the surface on which the vehicle travels for a given weather condition may be retrieved from data storage or received from a server, for example, based on the location of the vehicle. Maps of intensity of laser data per road distribution can be generated and stored for both dry and wet conditions. The distribution of expected values of laser data can be based on a composition of the surface. Based on a difference between the determined distribution and the laser data collected for the environment of the vehicle being above a threshold, an identification of a second indication of the weather condition can be made. For instance, if the difference is high for laser data that does not match that as expected to be seen for dry surface, such comparisons can be indicative of another indication that the surface is wet.

Within examples, using the method 300, the vehicle may be configured to operate in an autonomous mode, and the indication of the weather condition can be utilized to determine a driving decision for the vehicle. It may be desired to control the vehicle differently due to various weather conditions or conditions of the road, and thus, when the road is wet, the vehicle may be operated according to a "wet surface" driving technique (e.g., allow more space for braking, reduce speeds, etc.). Vehicles may not operate as well in certain weather conditions, and thus, in some examples, the vehicle may provide instructions to indicate a request to transition to a manual mode, such as by providing an alert to the driver to begin operation of the vehicle by disabling the autonomous mode.

In addition or as an alternative to making a driving decision, the road weather conditions and/or road surface conditions may trigger an alert to be sent to the driver. The alert may request the driver to take control of the vehicle or may simply provide an alert to the driver of the condition. The alert may be an aural signal, a visual signal, a haptic or tactile and/or any other signal that gets the attention of the driver. In this example, after alerting the driver, the vehicle may receive input from the driver, such as turning the steering wheel, applying the brake, applying the accelerator, pressing an emergency shut-off, etc.

In further examples, determinations of how wet the road is, how foggy the weather is, or how sunny the sky is can be made based on how many unassociated laser data points are present. In instances in which the road is very wet, there may be a large number of unassociated laser data points. A mode in which the vehicle operates may be further based on how wet road, such as for damp roads, the autonomous mode may be employed and for instances in which the road is deemed very wet, the vehicle may transition or provide a request to transition to a manual mode of operation.

In addition or as an alternative to making a driving decision, the weather conditions may cause changes to settings of sensors of the vehicle. For example, an exposure setting of the camera can be altered based on the indication that the weather condition of the environment of the vehicle is sunny, or settings of the LIDAR unit can be altered to lower exposure times. Additional actions can be taken as well, such as to deploy a visor or sun shade based on the identification.

In some examples, additional data may be considered (in addition to laser data points being unassociated with tracked objects) to provide further indications of the weather condition, or to provide a higher probability or confidence of a specific weather condition (e.g., that the unassociated laser data points are due to water).

Figure 4:
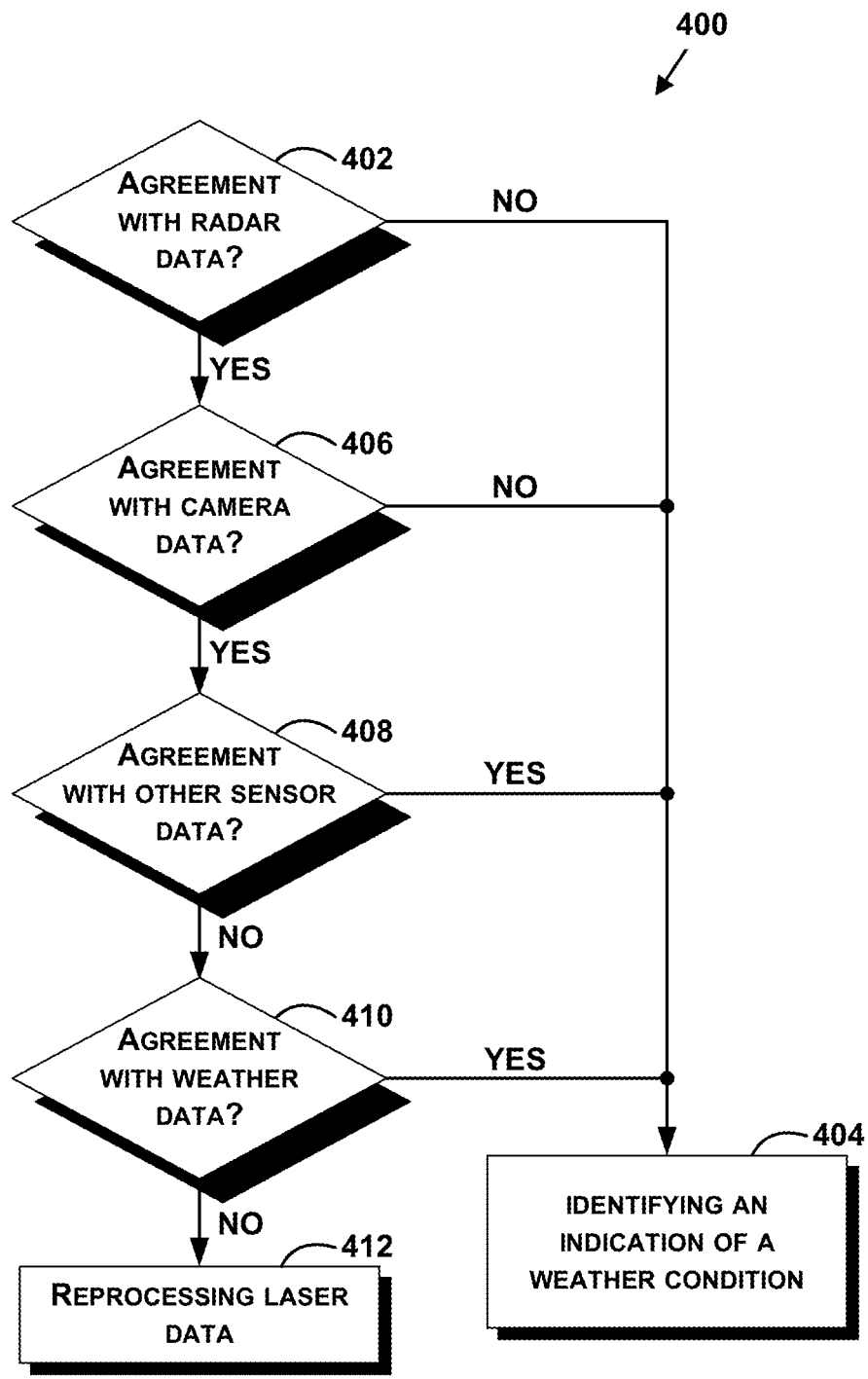
FIG. 4 is a block diagram of example methods for determining further indications of weather conditions using onboard vehicle sensors, in accordance with at least some embodiments described herein.

FIG. 4 is a block diagram of example methods for determining further indications of weather conditions using onboard vehicle sensors, in accordance with at least some embodiments described herein. Method 400 shown in FIG. 4 presents an embodiment of a method that, for example, could be used with the vehicle 100 and/or vehicle 200 as illustrated and described in reference to FIGS. 1 and 2, respectively (or components of the vehicle 100 or vehicle 200), and may be executed in addition to the method 300 shown in FIG. 3. The method 400 may represent a module, a segment, or a portion of program code, which includes one or more instructions (e.g., machine readable code) executable by a processor for implementing specific logical functions or steps in the process.

As shown at block 402, the method 400 may include determining whether the laser data is in agreement with RADAR data, and if not, the method 400 includes at block 404 identifying an indication of a weather condition. For example, the autonomous vehicle may collect radar data for the environment of the vehicle, and the RADAR data is indicative of a presence of objects in the environment of the vehicle. A radar will not return data for water kicked up, or fog, or sunlight, however, the radar data will identify a car in front of the autonomous vehicle. The laser data is also used to track objects as well as described above, and when the presence of an object as indicated by the RADAR data does not agree with the presence of an object as indicated by the LIDAR data, then the LIDAR data may be deemed to be incorrect. Any additional objects indicated by the LIDAR data that are not indicated by the RADAR data can be indicators of certain weather conditions, and to determine the specific weather condition, further processing of the method 400 may be performed.

In some examples, any objects tracked by the LIDAR data that are not seen in the RADAR data may be categorized as due to a weather condition. As shown in the method 400, based on a lack of agreement of the RADAR and LIDAR data, an indication of the weather condition can be made. The method 400 may further include making a determination as to whether a number of false matches is above a threshold. For example, for a small number of false returns, such as spurious or erroneous reflected laser data, no further action may be taken or the laser data can be reprocessed (as shown at block 412). However, when the number of false returns is above the threshold, the method can include identifying the weather condition.

In further examples, laser data points that are unassociated with objects as indicated by the RADAR that form a circular shape around objects indicated by the RADAR can be determined to be due to fog. In some examples, a density of the fog may also be estimated. For example, a distance between an object in the environment that is unassociated with laser data points (e.g., a fog) and a given object in the environment indicated by the radar data (and also possibly associated with laser data points) can be determined, and an estimation of a density of the fog can be made based on the distance. Using the two sensors (LIDAR and RADAR), a presence of an object at a certain range can be detected, and the distance between where the fog is detected to where the object is located can provide a measurement of visibility or density of the fog. Density may be stated as a distance of visibility, such as visibility of less than 5 km, for example, and the distance can be that as determined between where the fog is detected and where the object is located. In still further example, a determination of a density of the fog may be based on a number of unassociated laser data points. In instances in which a heavy or dense fog is present, there may be a large number of unassociated laser data points.

The method 400 may proceed to block 406 where the method 400 includes determining whether the laser data is in agreement with camera data. For example, the autonomous vehicle may include a camera and may receive image data collected for the environment of the vehicle. In heavy rains, water may build up on roadways, and may be visible in images. In addition, it may be possible to identify rain in the images as well. Images may be processed using object detection techniques, e.g., by providing the images to an object detection server and receiving a response indicating objects in the images. Thus, in some examples, the image data may be processed to identify the wet surface, and when the objects as indicated by the camera do not agree with objects as indicated by the LIDAR data, an indication that a surface on which the vehicle travels is wet can be made.

In further examples, image data may be processed to determine an amount of the image data that includes reflections of objects in the environment of the vehicle. For example, when it is raining, brake lights and other objects on the road provide reflections within images. Any number of techniques may be used to detect reflections in image, such as by analyzing motion trajectories of feature points and modeling reflections as regions containing two different layers moving over each other, for example. Based on the amount of the image data being indicative of reflections of the one or more objects in the environment of the vehicle being above a threshold, a second indication can be made that the surface on which the vehicle travels is wet. For other weather conditions, such as a fog, the fog may be visible in images, and thus, images may be processed using object detection techniques, e.g., by providing the images to an object detection server and receiving a response indicating objects in the images.

The method 400 may proceed to block 408 where the method 400 includes determining whether the laser data is in agreement with other sensor data. For example, the autonomous vehicle may have a precipitation sensor or "rain detector", and when the LIDAR data is indicative of a wet surface combined with the precipitation sensor indicating the presence of precipitation, a second indication can be made that the surface on which the vehicle travels is wet or the weather is rainy. It may not be possible to rely solely on outputs of the precipitation sensor to determine whether the surface is wet since the surface may remain wet for some time after it has stopped raining, or the surface may be wet due to puddles or other buildup of water when it is not raining.

In further examples, processing data provided by the various sensors may include processing environmental data that was obtained at a previous point in time and is expected to persist in the environment. For example, detailed map information (e.g., highly detailed maps identifying the shape and elevation of roadways, intersections, crosswalks, speed limits, traffic signals, buildings, signs, real time traffic information, or other such objects and information) may be provided or accessed via a database and may include data describing expected brightness or laser intensity data values for different stretches of roadway. When laser data does not match with expected brightness or laser intensity data values, indications of wet surfaces can be determined.

The method 400 may proceed to block 410 where the method 400 includes determining whether the laser data is in agreement with weather data. For example, weather information for a location of the vehicle can be received from a server over a network, and when the weather information indicates that it is raining or has rained recently, a second indication that the roadway is wet can be made based on the weather information. When the weather information indicates high temperatures, low clouds, or sunny conditions, a second indication that the environment is sunny can be made. When the weather information indicates a chance of fog, or foggy conditions, a second indication that a fog is present can be made. In further examples, additional weather data such as a temperature or dew point, can be determined from on-board vehicle sensors or communication with a server, and a second indication that the weather condition of the environment of the vehicle includes the fog can be made based on the temperature or dew point. For example, a fog may form when a difference between temperature and dew point is about less than 2.5 degrees Celsius or 4 degrees Fahrenheit. Fogs normally occur at a relative humidity near 100%, however, fogs can form at lower humidities, and fog can sometimes not form with relative humidity at 100%. A reading of 100% relative humidity means that the air can hold no additional moisture; the air will become supersaturated if additional moisture is added. Fogs can form suddenly, and can dissipate just as rapidly, depending what side of the dew point the temperature is on.

The method 400 may proceed to block 412 where the method 400 includes reprocessing the laser data to attempt to compare identified objects with those identified by a tracking system. The method 400 may further include confirming a determination of the weather condition based on access to information as determined by other cars on the road, for example.

Within examples, the method 400 may be optionally performed in addition to the method 300 in FIG. 3. For example, the unassociated laser points (e.g., representing untracked objects) could be unassociated relative to laser-detected vehicles or possibly unassociated relative to radar-detected vehicles, and the basis for identifying the weather condition may be verified by cross-reference to other sensor data, weather information, etc.

Figure 5:
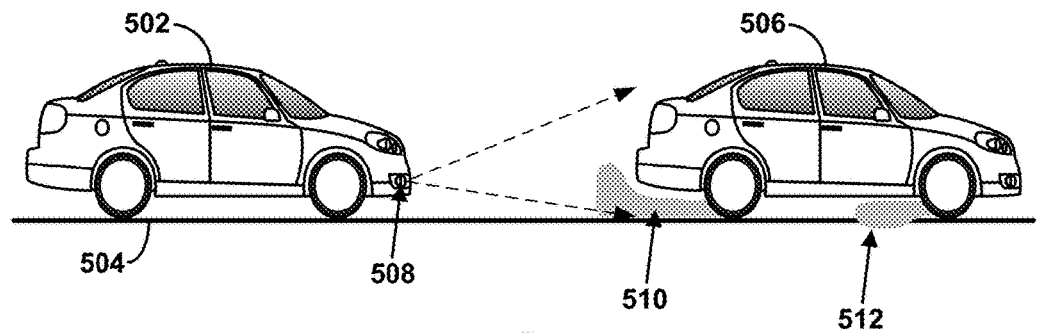
FIG. 5 is an example conceptual side view illustration of identifying a weather condition including an indication that a surface on which a vehicle travels is wet.

FIG. 5 is an example conceptual side view illustration of identifying a weather condition including an indication that a surface on which a vehicle travels is wet. In FIG. 5, a vehicle 502 travels on a surface 504 and another vehicle 506 travels in front of the vehicle 502. The vehicle 502 may include a LIDAR unit 508 that is configured to receive laser data collected for an area in front of the vehicle 502 (e.g., as shown by the arrows in FIG. 5). The vehicle 506 may travel through a puddle or other buildup of liquid/water on the surface 504, and may kick up water at a rear 510 of the vehicle 506 and/or at a side 512 of the vehicle 506. The water may be detected by the LIDAR unit 508 when laser beams are reflected by the water. However, the water may not be an object tracked by a tracking system of the vehicle 502, since other sensors (e.g., RADAR) may not detect the water or the LIDAR unit 508 may not track the water constantly over time. When laser data is received that does not match to tracked objects, the unassociated laser data can be deemed an indication of water, and an indication that the surface 504 is wet. The laser data may be compared to a predefined or stored rooster tail shape point cloud that may be generated due to water kicked up behind moving objects. The rooster tail water may be detected as laser reflections, but is not a tracked object in the environment, for example.

Thus, the vehicle 502 may identify an indication that the surface 504 is wet by detecting whether water is being kicked up by a vehicle's tires via processing of the unassociated or random laser points collected from the rear of the vehicle 506. In this regard, the vehicle 502 may detect a cloud or clouds of random data points behind rear tires of the vehicle 506, and as a consequence of the moving water, a location and number of the data points within the clouds may constantly be changing. Thus, a cloud of data points from water may not have a definitive structure, whereas a portion of solid object, such as the rear end of a vehicle, would be associated with data points defining a clear surface. Similar data point clouds may also be observed behind other vehicles. Such observations may indicate that it is raining or the ground is wet.

Figure 6:
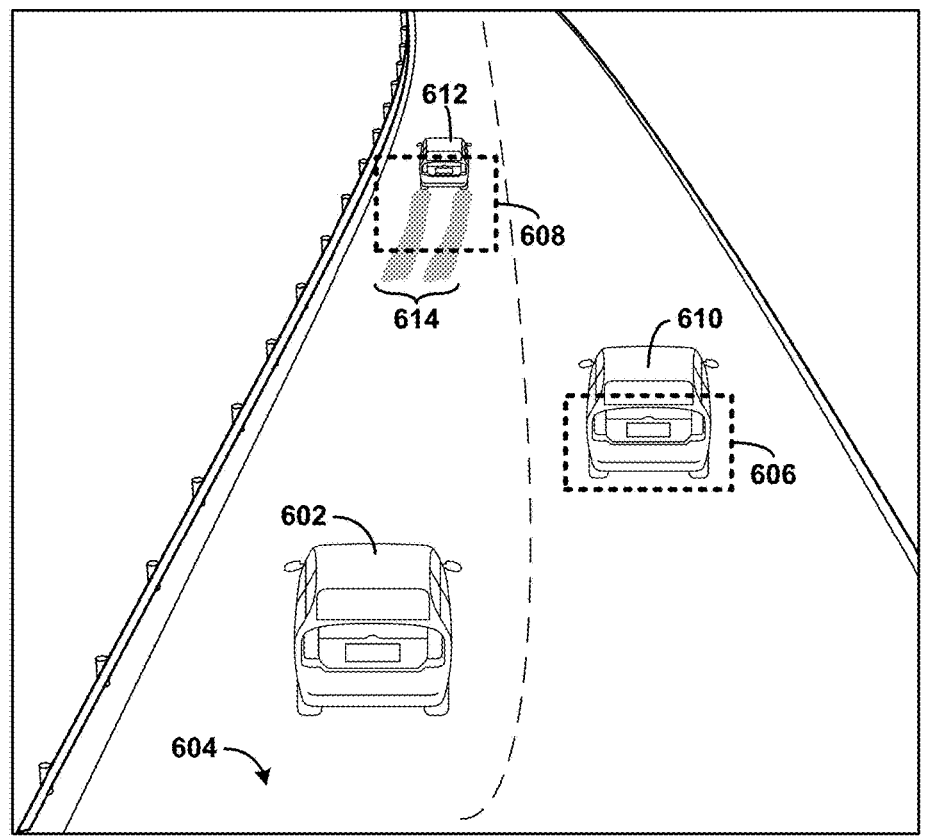
FIG. 6 is another example conceptual illustration of identifying an indication that a surface on which a vehicle travels is wet.

FIG. 6 is another example conceptual illustration of identifying an indication that a surface on which a vehicle travels is wet. In FIG. 6, a vehicle 602 travels on a surface 604 and includes sensors that collect data of areas around the vehicle 602. The sensors may include a LIDAR unit that can receive reflected laser beams from areas in the environment, such as from areas 606 and 608. The area 606 may be tracked and deemed indicative of another vehicle 610 traveling in front of and to the right of the vehicle 602. The area 608 may be tracked and deemed indicative of a vehicle 612 in front of the vehicle 602. Laser data collected for the area 608 may also be due to other items in the area 608, such as water tracks 614 on the surface 604 due to the vehicle 612 traveling through water. The water tracks 614 may be further seen within image data collected by sensors of the vehicle 602. The vehicle 602 could still further include a radar unit to determine a presence and a measurement of speed of the vehicle 612. The radar may not detect the water tracks 614. Since the radar determine the presence and speed of the vehicle 612 above a threshold, now that the laser data is indicative of some item (e.g., water tracks 614), then the vehicle 602 can come to the conclusion that the surface 604 substantially in front of the vehicle 602 is wet. However, if the speed of the vehicle 612 was low, such as a few miles per hour, then water may not be kicked up or water tracks may not be created, and thus, the laser data that is unassociated with other objects in the area 608 may be deemed to be spurious data.

FIG. 7 is another example conceptual illustration of identifying a weather condition that includes fog. In FIG. 7, a vehicle 702 travels on a surface and another vehicle 704 travels in front of the vehicle 702. The vehicle 702 may include a LIDAR unit 706 that is configured to receive laser data collected for an area in front of the vehicle 702 (e.g., as shown by the arrows in FIG. 7), and the laser data may indicate that the vehicle 704 is a at distance $d_1$ from the vehicle 702. The vehicle 704 may travel through a fog. The water in the fog may be detected by the LIDAR unit 706 when laser beams are reflected by the water, and the laser data may now indicate that the vehicle 704 is at a distance $d_2$ from the vehicle 702 due to the fog. However, the water may not be an object tracked by a tracking system of the vehicle 702, since other sensors (e.g., RADAR) may not detect the water or the LIDAR unit 708 may not track the water constantly over time. When laser data is received that does not match to tracked objects, the unassociated laser data can be deemed an indication of water in the air, and an indication that a fog is present.

The laser data may be compared to a predefined or stored shape point cloud that may be generated due to a fog. As an example, laser data points that are approximately around a tracked object, as indicated by the radar data, that are representative of an objects of a substantially circular shape that has a radius of a fog (when compared to stored point clouds) can be processed by comparison to stored point clouds for further verifications of the fog. For all laser data points unassociated with an object in the environment indicated by the radar data that are representative of objects approximately around a tracked object, such laser data points may be indicative of the fog. In this regard, the vehicle 702 may detect a cloud or clouds of random data points at a rear of the vehicle 704, and as a consequence of the moving water in the air, a location and number of the data points within the clouds may constantly be changing. Thus, a cloud of data points from a fog may not have a definitive structure, whereas a portion of solid object, such as the rear end of a vehicle, would be associated with data points defining a clear surface. Similar data point clouds may also be observed behind other vehicles. Such observations may indicate that a fog is present.

FIG. 8A is another example conceptual illustration of identifying an indication that a weather condition of the environment includes fog. In FIG. 8A, a vehicle 802 travels on a surface and includes sensors that collect data of areas around the vehicle 802. The sensors may include a LIDAR unit that can receive reflected laser beams from areas in the environment and a camera that can be configured to collect images of the environment. Another vehicle 804 may be traveling in front of the vehicle 802. The camera may capture an image of the area 806.

FIG. 8B is an example conceptual illustration of an image captured by the vehicle 802 in FIG. 8A. The image illustrates that a portion of a rear of the vehicle is covered or obscured by a fog. The image may be processed to determine that a number of pixels in the image data are substantially grey in color. Based on a percentage of the pixels being substantially grey in color, a second indication of a foggy weather condition may be made. In FIG. 8B, about 40-45% of the image is obscured by the fog, and thus, the threshold may be met. Lower percentages may be used as well. However, percentages of about 40% or more may be used for higher probabilities of the image including a fog.

In some examples, the image data may be processed to identify objects in the image, and when the objects as indicated by the camera image do not agree with objects as indicated by the LIDAR data, an indication that a fog is present can be made as well. For example, the image in FIG. 8B may indicate an object present in an area covering coordinates $x_1$-$x_n$, while the laser data may only indicate an object present in an area covering coordinates $x_2$-$x_n$. Thus, the camera data does not agree with the laser data, and such disagreement can be used as an indicator of a fog being present.

FIG. 9A is another example conceptual illustration of identifying a weather condition, which in this instance, is a sunny condition based on camera images. In FIG. 9A, a vehicle 902 travels on a surface and includes sensors that collect data of areas around the vehicle 902. The sensors may include a LIDAR unit that can receive reflected laser beams from areas in the environment and a camera that can be configured to collect images of the environment. Another vehicle 904 may be traveling in front of the vehicle 902. The camera may capture an image of the area 906.

FIG. 9B is an example conceptual illustration of an image captured by the vehicle 902 in FIG. 9A. The image illustrates that a portion of a rear of the vehicle is covered or obscured by sun rays. The image may be processed to determine that a number of pixels in the image data are substantially brighter in color than other pixels, or to determine that a number of pixels obscured by sun rays are substantially brighter in color as compared to a threshold value. Based on a percentage of the pixels being substantially above a predetermined color, a second indication of a sunny weather condition may be made. In FIG. 9B, about 50-55% of the image includes sun rays, and thus, the threshold may be met. Lower percentages may be used as well.

FIG. 10 includes another example conceptual side view illustration of identifying an indication that an environment of a vehicle is sunny. In FIG. 10, a vehicle 1002 travels on a surface and another vehicle 1004 travels in front of the vehicle 1002. The vehicle 1002 may include a LIDAR unit 1006 that is configured to receive laser data collected for an area in front of the vehicle 1002 (e.g., as shown by the arrows in FIG. 10), and the laser data may indicate that the vehicle 1004 is a at distance $d_1$ from the vehicle 1002. The environment may be sunny, as shown in FIG. 10, and the LIDAR unit 1006 may receive reflections due to the sun. Such reflections may be representative of false objects in the environment, such as object 1008 shown in FIG. 10. However, the object 1008 may not be an object tracked by a tracking system of the vehicle 1002, since other sensors (e.g., RADAR) may not detect the object 1008 or the LIDAR unit 1008 may not track the object 1008 constantly over time. When laser data is received that does not match to tracked objects, the unassociated laser data can be deemed to be due to sun reflections resulting in an indication that the environment of the vehicle is sunny.

Locations of collected laser data may be compared to predefined or stored locations that may be representative of objects resulting from sun reflections. As an example, laser data points that are approximately above a tracked object, as indicated by the radar data, or that are representative of objects of a substantially circular shape (when compared to stored point clouds) can be processed by comparison to stored point clouds for further verifications of objects due to sun reflections. In this regard, the vehicle 1002 may detect a cloud or clouds of random data points at around the vehicle 1004, and a location and number of the data points within the clouds may constantly be changing. Thus, a cloud of data points due to sun reflections may not have a definitive structure, whereas a portion of solid object, such as the rear end of a vehicle, would be associated with data points defining a clear surface. Similar data point clouds may also be observed behind other vehicles. Such observations may indicate that the environment is sunny.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

What is claimed is:

1. A method comprising:
   receiving laser data collected for an environment of a vehicle, wherein the laser data includes a plurality of laser data points;
   associating, by a computing device, laser data points of the plurality of laser data points with one or more objects in the environment;
   determining given laser data points of the plurality of laser data points that are unassociated with the one or more objects in the environment as being representative of an untracked object;
   receiving additional data collected for the environment of the vehicle from one or more additional sensors, wherein the additional data is indicative of a presence of one or more objects in the environment of the vehicle;
   determining laser data points of the plurality of laser data points that are associated with the one or more objects in the environment indicated by the additional data;
   based on laser data points being unassociated with the one or more objects in the environment indicated by the additional data, identifying by the computing device an indication of a weather condition in the environment; and
   controlling the vehicle in an autonomous mode based on the indication of the weather condition.

2. The method of claim 1, wherein receiving the laser data collected for the environment of the vehicle comprises receiving the laser data collected by performing one or more scans of the environment, and the method further comprises:
   tracking the one or more objects in the environment as the vehicle moves through the environment based on laser data received in the one or more scans of the environment.

3. The method of claim 1, further comprising:
   for a first scan of the environment, associating, by the computing device, the laser data points of the plurality of laser data points with one or more objects in the environment;
   for a second scan of the environment, determining laser data points that match to the one or more objects based on a location of an object represented by the laser data points; and
   determining the given laser data points that are unassociated with the one or more objects in the environment based on a lack of a match to the one or more objects in the first scan.

4. The method of claim 1, wherein identifying by the computing device the indication of the weather condition of the environment comprises:
   determining that a number of the given laser data points unassociated with the one or more objects in the environment is above a threshold number.

5. The method of claim 1, further comprising:
   receiving radar data collected for the environment of the vehicle, wherein the radar data is indicative of a presence of one or more objects in the environment of the vehicle;
   determining laser data points of the plurality of laser data points that are associated with the one or more objects in the environment indicated by the radar data; and
   based on laser data points being unassociated with the one or more objects in the environment indicated by the radar data, identifying the indication of the weather condition of the environment.

6. The method of claim 1, further comprising:
   receiving image data captured from a camera coupled to the vehicle; and
   identifying a second indication of the weather condition of the environment based on the image data.

7. The method of claim 1, further comprising:
   receiving weather information for a location of the vehicle from a server over a network; and
   identifying a second indication of the weather condition of the environment based on the weather information.

8. The method of claim 1, further comprising:
   receiving a current temperature for a location of the vehicle from a server over a network; and
   identifying a second indication of the weather condition of the environment based on the current temperature.

9. The method of claim 1, further comprising:
   receiving precipitation data from a precipitation sensor coupled to the vehicle; and
   identifying a second indication of the weather condition of the environment based on the precipitation data.

10. The method of claim 1, wherein the vehicle is configured to operate in an autonomous mode, and the method further comprises based on the indication of the weather condition of the environment, determining a driving decision for the vehicle.

11. The method of claim 1, further comprising:
determining a speed of the vehicle, and
wherein identifying by the computing device the indication of the weather condition of the environment includes identifying that a surface on which the vehicle travels is wet based on the speed of the vehicle being above a threshold.

12. The method of claim 1, further comprising:
comparing the given laser data points that are unassociated with the one or more objects in the environment with stored laser data points representative of a pattern due to fog; and
based on the comparison, identifying by the computing device the weather condition of the environment to include fog.

13. The method of claim 1, further comprising:
determining that the given laser data points of the plurality of laser data points that are unassociated with the one or more objects in the environment are representative of an untracked object at a given position with respect to the vehicle;
determining that the untracked object remains at a substantially same relative position with respect to the vehicle as the vehicle moves; and
identifying by the computing device the weather condition of the environment to be sunny.

14. The method of claim 1, further comprising:
determining a geographic location of the vehicle and a time of day;
based on the geographic location of the vehicle and the time of day, determining an approximate position of the sun relative to the vehicle; and
identifying by the computing device a second indication of the weather condition of the environment based on the approximate position of the sun relative to the vehicle.

15. The method of claim 1, wherein the weather condition includes one or more of wetting of a roadway, a fog or sunlight.

16. The method of claim 1, wherein controlling the vehicle in an autonomous mode based on the indication of the weather condition comprises transitioning vehicle control to a manual mode.

17. A non-transitory computer readable storage medium having stored therein instructions, that when executed by a computing device, cause the computing device to perform functions comprising:
receiving laser data collected for an environment of a vehicle, wherein the laser data includes a plurality of laser data points;
associating laser data points of the plurality of laser data points with one or more objects in the environment;
determining given laser data points of the plurality of laser data points that are unassociated with the one or more objects in the environment as being representative of an untracked object;
receiving additional data collected for the environment of the vehicle from one or more additional sensors, wherein the additional data is indicative of a presence of one or more objects in the environment of the vehicle;
determining laser data points of the plurality of laser data points that are associated with the one or more objects in the environment indicated by the additional data;
based on laser data points being unassociated with the one or more objects in the environment indicated by the additional data, identifying by the computing device an indication of a weather condition in the environment; and
controlling the vehicle in an autonomous mode based on the indication of the weather condition.

18. The non-transitory computer readable storage medium of claim 17, wherein receiving the laser data collected for the environment of the vehicle comprises receiving the laser data collected by performing one or more scans of the environment, and the functions further comprise:
tracking the one or more objects in the environment as the vehicle moves through the environment based on laser data received in the one or more scans of the environment.

19. The non-transitory computer readable storage medium of claim 17, wherein controlling the vehicle in an autonomous mode based on the indication of the weather condition comprises transitioning vehicle control to a manual mode.

20. A system, comprising:
at least one processor; and
data storage comprising instructions executable by the at least one processor to cause the system to perform functions comprising:
receiving laser data collected for an environment of a vehicle, wherein the laser data includes a plurality of laser data points;
associating laser data points of the plurality of laser data points with one or more objects in the environment;
determining given laser data points of the plurality of laser data points that are unassociated with the one or more objects in the environment as being representative of an untracked object;
receiving additional data collected for the environment of the vehicle from one or more additional sensors, wherein the additional data is indicative of a presence of one or more objects in the environment of the vehicle;
determining laser data points of the plurality of laser data points that are associated with the one or more objects in the environment indicated by the additional data; and
based on laser data points being unassociated with the one or more objects in the surrounding environment indicated by the additional data, identifying an indication of a weather condition in the environment; and
controlling the vehicle in an autonomous mode based on the indication of the weather condition.

21. The system of claim 20, wherein the vehicle is traveling along a roadway, and the functions further comprise:
receiving radar data collected for the environment of the vehicle, wherein the radar data is indicative of a presence of one or more objects in the environment of the vehicle;
determining laser data points of the plurality of laser data points that are associated with the one or more objects in the environment indicated by the radar data; and
based on laser data points being unassociated with the one or more objects in the environment indicated by the radar data, identifying the indication of the weather condition of the environment.

22. The system of claim 20, wherein the weather condition includes one or more of wetting of a roadway, a fog or sunlight.

23. The system of claim 20, wherein controlling the vehicle in an autonomous mode based on the indication of the weather condition comprises transitioning vehicle control to a manual mode.

* * * * *